United States Patent [19]
Glassman

[11] Patent Number: 5,105,457
[45] Date of Patent: Apr. 14, 1992

[54] MAMMOGRAPH X-RAY GRID

[76] Inventor: Stuart L. Glassman, 103 Timbercreek Rd., Hendersonville, N.C. 28739

[21] Appl. No.: 511,045

[22] Filed: Apr. 19, 1990

[51] Int. Cl.⁵ .............................................. H05G 1/28
[52] U.S. Cl. .................... 378/163; 378/164; 378/180; 378/37; 378/208
[58] Field of Search ............... 378/20, 37, 163, 208, 378/180, 162–164; 128/653, 659, 664

[56] References Cited

U.S. PATENT DOCUMENTS

| | | | |
|---|---|---|---|
| 2,344,824 | 3/1944 | Landis et al. | 378/164 |
| 3,111,582 | 11/1963 | Levi | 378/164 |
| 3,547,121 | 12/1970 | Cherry | 378/164 |
| 4,691,333 | 9/1987 | Gabriele et al. | 378/37 |
| 4,837,795 | 6/1989 | Garrigus | 378/37 |
| 4,860,331 | 8/1989 | Williams et al. | 378/163 |
| 4,918,715 | 4/1990 | Krupnick et al. | 378/164 |

Primary Examiner—Janice A. Howell
Assistant Examiner—Kim-Kwok Chu
Attorney, Agent, or Firm—R. M. Saccocio

[57] ABSTRACT

Apparatus and methods are disclosed for efficiently and quickly determining the exact location of spicules of calcium within a test specimen of human tissue removed from a woman's breast. By exactly locating the clusters of calcification, a pathologist can dissect the portion of the test specimen containing the calcifications and quickly analyze the same to determine whether or not malignancy exists. A pair of grid plates is provided, one on top of the other, with clamping means to compress a test specimen therebetween in the present invention. The plates include a grid system which is opaque to radiographic filming which allows the determination of the exact location of the clusters of calcifications.

6 Claims, 2 Drawing Sheets

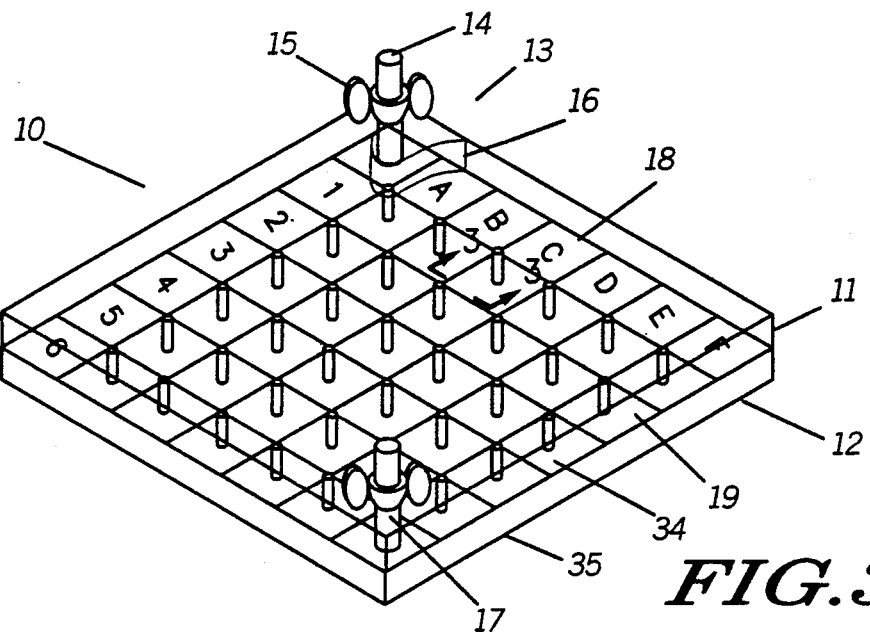
FIG.1
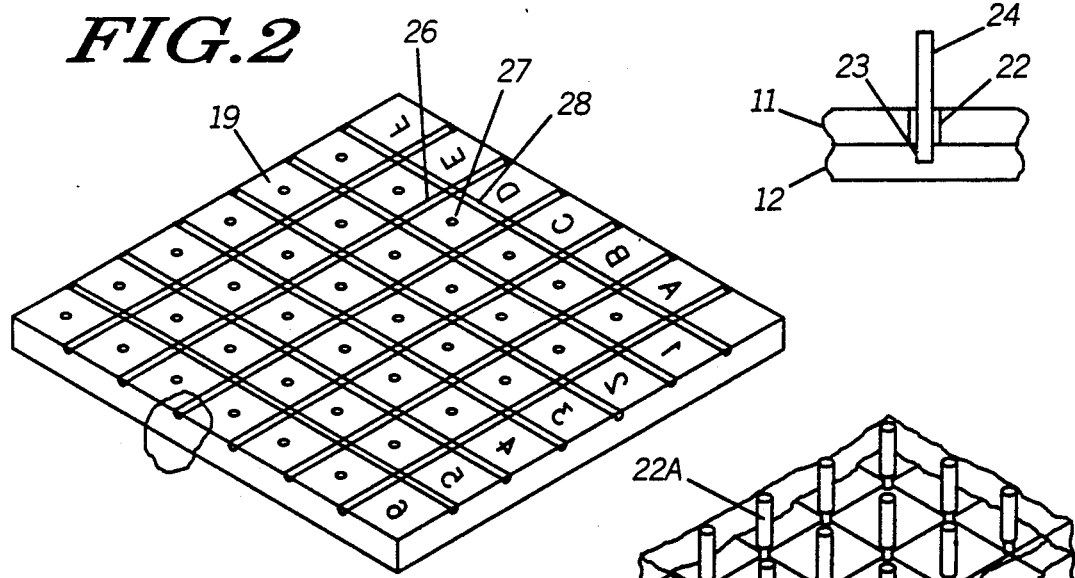
FIG.2
FIG.3
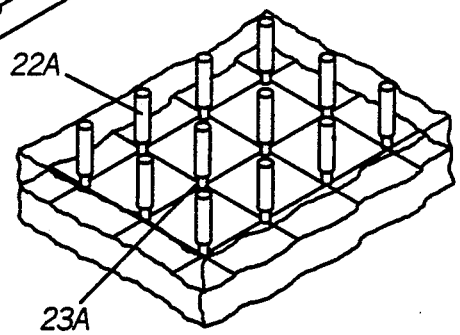
FIG.4
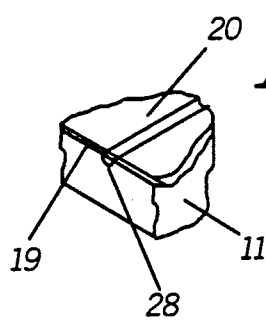
FIG.2A
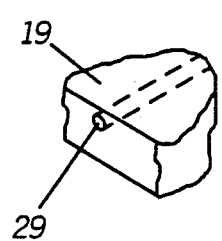
FIG.2B

MAMMOGRAPH X-RAY GRID

BACKGROUND OF THE INVENTION

1. Field of the Invention

This invention pertains in general to the field of medical x-ray diagnostics and in particular to the field of medical mammographs to detect early stages of cancer in a woman's breasts.

2. Description of the Prior Art

Breast cancer in women is, of course, a very serious medical problem. Once a malignancy is found, the typical medical procedure is to remove one or both breasts immediately. Should the malignancy continue to spread because the cancer has not been earlier diagnosed or the removal operation occurred too late, the result can be fatal. Accordingly, the earliest possible detection of breast cancer and the earliest possible removal of the malignancy is of the utmost urgency.

Certain types of breast cancer which is in a later stage of development can easily be determined by a physical examination of the breasts to determine the presence of lumps. Once such lumps are determined to exist, the next step is to perform a biopsy to determine if the lump is malignant or benign. Should the lump be malignant, the remedy is, of course, partial removal of the portion of the breast which contains the lump or complete removal of one or both of the breasts. Since the presence and location of the lump is readily ascertainable by a physical examination, removal of the lump for biopsy examination is a relatively simple task. However, should the cancer be in an earlier stage of development, the detection thereof, the exact location thereof within the breasts, and the removal of the same for immediate biopsy examination become difficult tasks.

The early stages of malignancy or cancer in a breast manifests itself by a cluster of microcalcifications which comprise a plurality of spaced fine spicules of calcium which are visible on a mammogram as very tiny dots. Since the spicules are comprised of calcium, they appear as light or undeveloped dots on the x-ray film.

Once such early signs of malignancy are determined by a mammogram, the roentgenologist, with the aid of fluoroscopy, physically locates the same within a breast by using a pair of very thin elongated needle wires under fluoroscopic guidance. In this regard the roentgenologist will insert one wire needle into the breast along a line parallel to the longitudinal axis of a person's body. Then, he will insert another wire into the breast at right angles to the first wire with the points of both wires being placed at the precise location of the cluster of microcalcifications. The surgeon then cuts into the breast and removes the portion of the breast tissue which he believes includes the cluster of microcalcifications. Once this sample is removed from the breast, the locating guide wires are, of course, removed therefrom. Typically, while the woman is still within the operating room and under anesthesia, the breast sample is then sent to the pathology laboratory where the sample is sandwiched between a pair of plates thereby compressing the sample tissue biopsy into a flattened shape. The flattened shape of the sample is then x-rayed and the film developed to determine the presence and location of the spicules of calcium. If spicules are not found with x-ray, the pathologist sends a message, or calls, the surgeon in the operating room and tells him he failed to remove that portion with the calcifications. The surgeon then has to remove more breast tissue which is again given to the pathologist who repeats the procedure of sandwiching the tissue sample and x-raying the same. Upon determining the presence and location of spicules, the sample is then frozen and cut into very fine slices (25/1000 of an inch) which may be placed under a microscope after a staining procedure and examined. Should the pathologist find that the tissue with calcifications are malignant, the results are immediately sent to the operating surgeon who then removes the appropriate portion or the entire breast or breasts of the patient.

In accordance with the above it is obvious that time is of the essence while the pathologist is preparing the sample of the breast tissue for x-ray examination and then preparing further samples for microscopic examination to determine if calcifications are present, and whether or not the sample is malignant. In the prior art the main constraining time factor involves locating the cluster of calcifications within the tissue sample and then sectioning that portion of the sample which contains the calcifications. Because the pathologist can only use a mammograph to determine the approximate location of the calcifications within the sample and because the sample tends to contract once the sandwiching pressure is removed, the pathologist can only guess where the calcifications are and must therefore prepare a larger than necessary number of slivers of the specimen for microscopic examination. During this relatively extended period of time, as mentioned above, the patient and the entire surgical operating team are patiently waiting in the operating room for the results of the biopsy examination of one and maybe more tissue specimens. Accordingly, new apparatus and methods are desirable to reduce the time of the pathological examination of the specimens.

Accordingly, a primary object of the present invention is to provide apparatus and methods which significantly shorten the time between the removal of a test sample of a patient's breast suspected of containing early stages of cancer and the microscopic examination of the same to determine if malignancy exists.

Another object of the present invention is to significantly shorten the time of a biopsy examination of a test portion of a person's breasts suspected of containing early calcifications found in early stages of cancer.

Another object of the present invention is to provide apparatus and methods which allows a pathologist to rapidly locate and remove a small portion of a large test specimen, which small portion is suspected to contain early stages of cancer.

The above-stated objects as well as other objects which, although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The present invention accomplishes the above-stated objectives as well as others, as may be determined by a fair reading of this specification which comprises a mammograph x-ray grid apparatus and methods for locating a specific portion of a biopsy specimen of a person's breast which is known to contain spicules of calcium and thereby allow quick and efficient biopsy examination.

In accordance with the present invention, a pair of plates having a substantially square configuration are provided with a means of compressing a sample of human tissue placed between the plates into a flattened and expanded form. The clamping means may comprise a plurality of bolts and nuts located at edge portions of the plates which allow for tightening of the same and thereby compressing the plates towards each other. One of the plates, preferably the top plate, is inscribed with a grid pattern at approximately the location of the underside surface thereof. The grid pattern is in grooves filled with a radiographic opaque material such as wire, lead, or barium so as to be clearly visible on mammographic x-ray. Each of the grid spaces are provided with holes at the center thereof or at the corners thereof so that one or more pins may be placed at the grid space which is determined to contain the microcalcifications. Upon separating of the two plates by removal of the upper plate therefrom, the one or more pins remain in position within the specimen so as to clearly locate the exact position of the calcifications. Thereafter, it is a relatively simple task for the pathologist to cut away from the specimen the unnecessary portions thereof so as to leave a small square flattened portion thereof which does contain the calcifications. Then, the pathologist may divide the final test specimen into a number of thin slivers or sections for microscopic examination. In this manner, the portions of the test specimen which did not contain the calcifications are completely eliminated from the examination procedure and the time involved in the same is thereby saved.

BRIEF DESCRIPTION OF THE DRAWINGS

Various other objects, advantages, and features of the invention will become apparent to those skilled in the art from the following discussion taken in conjunction with the following drawings, in which:

FIG. 1 comprises an overall isometric view of the inventive apparatus showing two plates, one on top of each other, being secured by clamping means;

FIG. 2 comprises an isometric view of the top plate of FIG. 1 with the top plate being inverted to show the underside view thereof;

FIG. 2A comprises an isometric blown-up portion of the top plate of FIG. 2 illustrating a grid filled with a radiographic opaque material and a protective covering thereon;

FIG. 2B illustrates another embodiment of the apparatus of FIG. 2A;

FIG. 3 shows a blown-up cross-sectional view taken across the lines 3—3 of FIG. 1 illustrating pin holes in the plates and a pin located therein;

FIG. 4 depicts a location of the pin holes in the top plate different from the location of FIG. 1;

DESCRIPTION OF THE PREFERRED EMBODIMENTS

Figure 5:
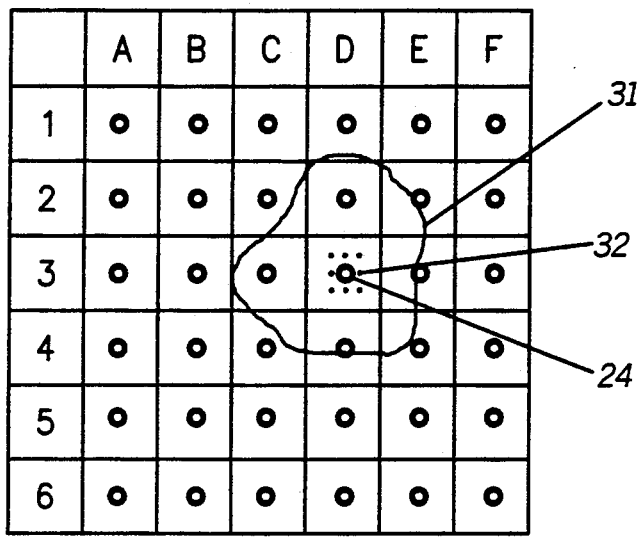
FIG. 5 shows a top plan view of a typical mammographic X-ray showing a test specimen therein containing a cluster of calcifications located at a particular grid space.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the numeral 10.

Referring now specifically FIG. 1 of the drawings, a top plate 11 and a bottom plate 12 each comprising a substantially square plate which may be placed one on top of the other. Clamping means 13 which may comprise a threaded bolt and wing nut combination is utilized to forcibly compress the top plate against the bottom plate when a test specimen is located therebetween. In the embodiment of FIG. 1, a threaded bolt 14 is securely attached to the bottom plate 12 at a corner thereof with the longitudinal axis of the bolt perpendicular to the plane of the plate 12. Bolt 14 extends up through hole 17 at one corner of plate 11 and up through a swing-away space 16 at a diagonally opposite corner of plate 11. The combination of hole 17 and swing-away space 16 in top plate 11 allows the two plates 11 and 12 to remain connected to each other and allows the top plate 11 to be either swung away from bottom plate 12 or by the removal of wing nuts 15 allows top plate 11 to be removed in a perpendicular direction away from plate 12.

A grid pattern 18 is provided on the bottom surface 19 of plate 11. The top row of grid spaces may be designated as shown in FIG. 1A through 1F while a side row of grid pattern 18 may be designated with the numerals one through six. By cross-referencing the numerals with the letters any particular space within the grid may be individually designated. For example, the grid space D2 comprises the grid space marked with the "X" in FIG. 1. Thus, the entire bottom surface 19 of top plate is divided up into specifically designated grid spaces.

Each of the grid spaces at the center thereof includes a through hole 22 through top plate 11 in a transverse direction thereto and a hole 23 coaxial with hole 24 but in bottom plate 12. Hole 23 is smaller in diameter than hole 22 and does not go all the way through the thickness in bottom plate 12. This is clearly seen in FIG. 3 of the drawings. The providing of holes 22 and 23 and the sizing thereof permits a pin 24 to be placed through hole 22 and into hole 23. Pin 24 may be sized to fit snugly within hole 23 and therefore pass freely through hole 22. In this manner, when top plate 11 is removed from bottom plate 12, pin 24 will stay imbedded within hole 23 in bottom plate 12. FIG. 4 shows an alternate embodiment of the holes 22 and 23 of FIG. 1 of the drawings. In FIG. 4 holes 22A and 23A are provided in the upper 11 and lower plates 12, respectively, at the corners of each of the grid spaces. Holes 22A and 23A may be sized in accordance with holes 22 and 23 so as to permit a pin 24 to fit through hole 22A and be secured within hole 23A.

Grid lines 25 and grid lines 26 which run perpendicular to each other, and spaced from each other so as to provide a grid space 27 therebetween, are preferably filled with a radiographic opaque material or wire so as to clearly show the form of the grid pattern 18 on a mammographic x-ray film. Accordingly, grid lines 25 and 26 may be scribed into the bottom surface 19 of top plate 11 so as to form a small groove 28 therein. FIG. 2A shows a typical groove 28. Groove 28 may then be filled with a material such as barium or wire which is opaque to x-rays and therefore clearly shows on a developed film. In order to maintain the material 29 within grooves 28, a protective outer film 20 of an x-ray transparent material such as a hardenable liquid acrylic may be placed over bottom surface 19. In FIG. 2B the grid lines 25 and 26 comprise elongated strands of wire material such as barium imbedded within the top plate 11 just slightly under the underside surface 19 thereof. The placement of the letters A through F and the numerals one through six on the underside surface 19 of top plate 11 also comprise a material opaque to x-rays.

The apparatus depicted in FIGS. 1 through 4 and explained above may be utilized as follows. A woman has been typically diagnosed to have the possibility of the existence of an early form of cancer in one or both of her breasts. She may be located in a operating room with a surgical team in attendance. The suspect area of the woman's breast will have been located utilizing a typical wire needle localization technique. Being guided by the location of the needles within the woman's breast, the operating surgeon may then remove a test biopsy or specimen of the woman's breast at the location of the juncture of the two needles as well as a sufficient portion around the juncture to assure the surgeon that the portion removed contains the suspected spicules of calcium. The excised specimen is then sent to the radiology department for a specimen radiography which will determine whether or not the calcium spicules are present.

The specimen which appears to be a relatively large glob of fatty fibrous tissue is then placed on the upper surface of the bottom plate 12 at approximately the center thereof. Upper plate 11 is then placed over the specimen and such that the side edges of the two plates are approximately aligned with each other. Clamping means 13 are then utilized whereby wing nuts 15 are rotated clockwise to bring the plates 11 and 12 toward each other and in the meantime compress the relatively large glob of fatty fibrous tissue 32 in FIG. 5 between plates 11 and 12. Continued rotation of wing nuts 15 flattens out test specimen 31 to an appropriate thickness. Compression of the specimen is highly desirous inasmuch the compressed specimen results in a better and clearer x-ray picture. The entire grid 10 with the specimen 31 compressed therebetween is then x-rayed to confirm the presence of the calcifications within the excised specimen 31 and to determine the exact location of the calcifications therein. When the x-rays are developed and the presence of the calcifications has been confirmed, the exact location of the same may be determined by cross indexing the letters with the numerals such that, for example, in FIG. 5 grid space D3 contains the calcifications designated 32 in FIG. 5. As may be seen, the calcifications 32 appear as a cluster of dots in the x-ray film. Once the location of calcifications 32 has been determined relative to the overall size and shape of the test specimen 31, a pin 24 may be inserted into the center of grid space D3 so as to mark the location of the calcifications 32. Then, top plate 11 is removed from bottom plate 12 by manipulation of clamping means 13 and leaving the test specimen 31 pinned in place on the lower plate 12. Since the hole 22 in top plate 11 is larger in diameter than pin 24, the top plate 11 may be removed without disturbing the location of pin 24 in grid space D3.

Figure 6:
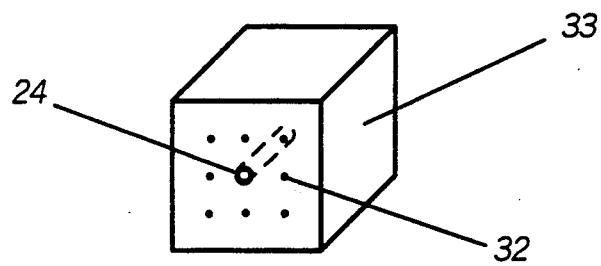
FIG. 6 shows the portion of the test specimen of FIG. 5 which contains the calcifications which location is determined by a center pin; and, FIG. 7 shows the portion of the test specimen of FIG. 5 which contains the calcifications which location is determined by corner pins of FIG. 4.
Figure 7:
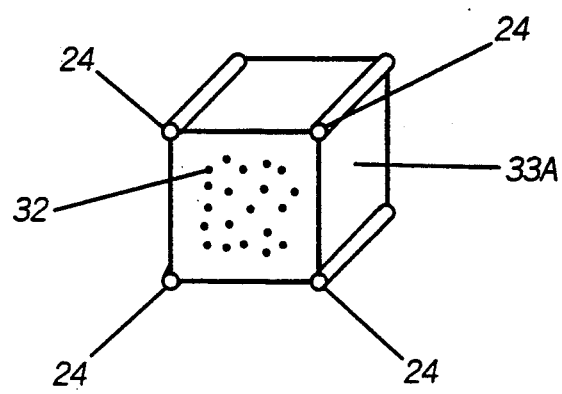

Once the top plate 11 is removed, the test specimen 31 will slightly contract due to the removal of the pressure. But, this effect will not affect determination of the location of the calcifications 32 by pin or pins 24. The specimen and the radiograph are then sent to a pathologist with the specimen still on the bottom grid plate and in the exact position in which it was filmed. The pathologist can then identify the exact location of the microcalcifications by its coordinates on the grid and using the center pins of the apparatus of FIG. 1 or the corner pins of the apparatus of FIG. 4. He may then thereafter section through the specimen still on the bottom grid plate 12 to define the exact square grid space D3 where the calcifications are seen and remove the grid space D3 portion away from the unnecessary outer portions of the overall test specimen 31. The resulting small biopsy specimen is shown in FIG. 6 as item 33 and in FIG. 7 as item 33A.

The pathologist then freezes the resulting small biopsy specimen 33 or 33A and thereafter sections the same into very thin transverse slivers or sections, each of which are stained so that they may be examined under a microscope. After examining only those specimens cut from small biopsy portion 33, the pathologist can make the determination whether or not the calcifications 32 are malignant. These results are then immediately sent to the surgeon and the patient waiting in the operating room. If indeed the calcifications were malignant, the operating surgeon proceeds to remove that portion or the entire breast as he determines is necessary.

In addition to the location of the grid lines 25 and 26 on the underside 19 of top plate 11, it may be desirable to scribe the same grid locations on the top surface 34 or the bottom surface 35 of bottom plate 12 as seen in FIG. 5. The grid lines on bottom plate 12, however, need not be filled with a radiographic opaque material. In fact it is preferred that no such material be utilized to fill the grid lines on bottom plate 12. Such lines would only interfere with the x-rays taken of the test specimen 31 when compressed between the top and bottom plates and 12, respectively. The location of grid lines on bottom plate 12, however, will aid the pathologist in dissecting the overall test specimen 31 to remove the unwanted portions thereof and leave the small biopsy test portion 33 or 33A. And, as stated above, the dissection of specimen 31 can take place while test specimen 31 is still on bottom plate 12.

Following removal of the resulting test specimen 33 or 33A from bottom plate 12, the remaining portions of the test specimen may be removed and discarded. Thereafter, the top 11 and bottom plates may be cleaned and made ready for subsequent use.

In prototype testing it has been determined that four-by-four inches square blocks of clear plexiglass, which are each one-quarter of an inch ($\frac{1}{4}$") thick, may be utilized for the top 11 and bottom 12 plates. Each of the grid spaces may be sized approximately one-half inch square. Other sizes of the plates 11 and 12 and the size of grid spaces 27 may also be used.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as my invention:

1. A method for determining the location of a cluster of calcifications within a test sample of human tissue comprising the steps of:

placing said sample of human tissue between a pair of parallel plates, placed one on top of the other, one of said pair of plates having a radiopaque grid arrangement forming a plurality of adjacent substantially square areas, compressing said sample of human tissue into a flattened shape between said plates, x-raying said plates with said test sample there between and determining the grid space or spaces within which said cluster of calcifications exist within said test sample, and marking said test sample at the location of the cluster of calcifications relative to said grid space or spaces by placing a pin or pins within holes provided within said plates.

2. Apparatus for determining the location of a cluster of calcifications within a sample of human tissue comprising:

a first plate and a second plate proportioned to fit one on top of the other, clamping means for flattening a sample of human tissue placed between said plates, a grid system having lines which are radiopaque and arranged to define a plurality of grid spaces, means for marking said test specimen at a location of the cluster of calcifications relative to said grid system, said marking means comprising a pin passing through one of said plates and through said test specimen into said second plate at said location of said cluster of calcifications, and said grid spaces comprising a plurality of spaced lines extending in a second direction perpendicular to said first direction to define a plurality of square spaces.

3. The apparatus of claim 2, wherein said clamping means comprises one or more threaded fasteners each including a tightening nut.

4. The apparatus of claim 2, wherein said marking means further comprises a hole in one of said plates having a diameter larger than the diameter of said pin and a hole in said second plate having substantially the same diameter as the diameter of said pin.

5. The apparatus of claim 4, wherein said marking means comprises said holes being located at approximately the center portion of a grid space defined by said grid lines.

6. The apparatus of claim 4, wherein said marking means comprises holes at the corners of said grid space as defined by said grid lines.

* * * * *